United States Patent [19]

Jackson

[11] 4,006,183

[45] Feb. 1, 1977

[54] SUBSTITUTED α-METHYLSULFINYL-O-TOLUIDINES

[75] Inventor: Thomas E. Jackson, Madison, N.J.

[73] Assignee: Sandoz, Inc., E. Hanover, N.J.

[22] Filed: July 8, 1975

[21] Appl. No.: 594,120

[52] U.S. Cl. .................. 260/558 S; 260/558 P; 260/578; 260/501.19; 260/501.21; 424/324; 424/330

[51] Int. Cl.$^2$ ............. C07C 103/78; C07C 87/56; A61K 31/165; A61K 31/135

[58] Field of Search .......... 260/558 S, 578, 501.19, 260/501.21

[56] References Cited

UNITED STATES PATENTS

| | | | |
|---|---|---|---|
| 3,576,872 | 4/1971 | Singhel | 260/578 X |
| 3,637,803 | 1/1972 | Shen et al. | 260/578 X |
| 3,689,567 | 9/1972 | Shen et al. | 260/578 X |
| 3,804,904 | 4/1974 | Bentley et al. | 260/578 X |
| 3,966,817 | 6/1976 | Pilgram | 260/578 |

OTHER PUBLICATIONS

Claus et al., Monat. Chemie 102, pp. 1571–1582 (1971).

*Primary Examiner*—Daniel E. Wyman
*Assistant Examiner*—Thomas A. Waltz
*Attorney, Agent, or Firm*—Gerald D. Sharkin; Richard E. Vila; Joseph J. Borovian

[57] ABSTRACT

The invention discloses optionally substituted α-methylsulfinyl-o-toluidines having pharmacological activity in animals and useful as CNS depressant agents. The compounds may be prepared by reacting an optionally substituted α-methylthio-o-toluidine with an oxidizing agent.

4 Claims, No Drawings

SUBSTITUTED α-METHYLSULFINYL-O-TOLUIDINES

The compounds α-methylsulfinyl-o-toluidine, 4-chloro-α-methylsulfinyl-o-toluidine and 4-chloro-6-methyl-α-methylsulfinyl-o-toluidine have been previously disclosed in the literature by P. Claus et al, Monatsh. Chem. 102, 1571-1582 (1971). To my knowledge, no pharmacological activity has been heretofore associated with any of these compounds.

The present invention relates to optionally substituted α-methylsulfinyl-o-toluidines and to their use as CNS depressant agents. The invention also relates to pharmaceutical compositions containing the above compounds as an active ingredient thereof and to the method of using such compositions as CNS depressants, particularly for inducing sleep and as tranquilizers.

The compounds of this invention may be represented by the following structural formula I:

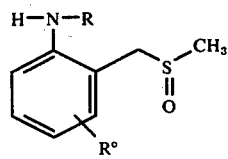

wherein
R° is hydrogen or $CF_3$, wherein said $CF_3$ is in the 3- or 4-position of the ring, and
R is hydrogen or meta- or paratrifluoromethylbenzoyl;
provided that when one of R° and R is hydrogen, the other is other than hydrogen.

The compounds of formula I may be prepared by the following reaction scheme:

PROCEDURE A

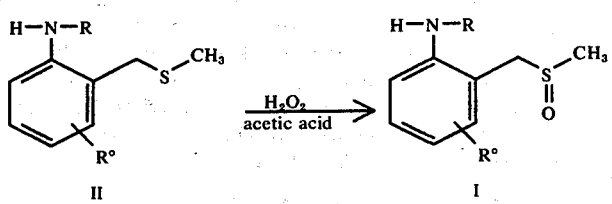

wherein R° and R are as defined above.

The preparation of compounds of formula I by Procedure A involves reacting an optionally substituted α-methylthio-o-toluidine of formula II above with hydrogen peroxide in the presence of acetic acid. The reaction may be carried out at temperatures in the range of from −20° C. to 70° C., preferably −5° C. to 25° C., and most preferably, between 0° C. and 10° C. Inclusion of a solvent is optional and may be any of those typically used in oxidation reactions, such as chlorinated hydrocarbons. The product is recovered using conventional techniques, e.g., crystallization.

The compounds of formula I may also be prepared according to the following reaction scheme:

PROCEDURE B

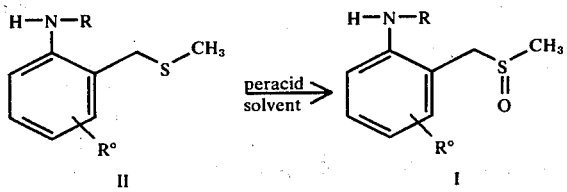

wherein R° and R are as defined above.

The preparation of compounds of formula I by Procedure B involves the reaction of an optionally substituted α-methylthio-o-toluidine of formula II above with not more than an equimolar amount of a peracid in the presence of an inert, organic solvent which is adapted to dissolving the reactants and product compounds of formula I. Suitable solvents are known and available, and include by way of illustration, the chlorinated hydrocarbons, lower alkanols, e.g., ethanol, and ethers, e.g., dioxane, tetrahydrofuran, etc. The reaction is preferably effected employing m-chloro-peroxybenzoic acid in the presence of a chlorinated hydrocarbon, e.g., methylene chloride. The reaction may be carried out at temperatures in the range of from −20° C. to 70° C., preferably −5° C. to 25° C., and most preferably, between 0° C. and 10° C. The reaction product of formula I may be isolated from the reaction mixture by working up by conventional techniques.

The compounds of formula II are either known or can be prepared in conventional manner from available materials, e.g., by the procedures of Gassman and Greutzmacher, J. Amer. Chem. Soc. 96 (17), 5487-5495 (1974) or by the procedures of Claus, Vycudilik and Rieder, Monatsh. Chem. 102, 1571-1582 (1971).

The compounds of formula I are useful because they possess pharmacological activity in animals. In particular, the compounds effect a depression of the central nervous system and are useful as sleep inducers and minor tranquilizers as indicated: 1) by the hexobarbital reinduction method of Winter, J. Pharmacol. and Exp. Therap., 94, 7-11, 1948; 2) by their ability to produce docility in behavior tests in mice given 10 to 200 mg./kg. i.p. of test compound according to the 30-word adjective check sheet system, basically described by S. Irwin, Gordon Research Conference, Medicinal Chemistry, 1949 and Chem. Symposium on Sedative and Hypnotic Drugs, Williams and Wilkins, 1954; 3) by their ability to antagonize chronic convulsions and death in mice given 45 to 250 mg./kg. i.p. of N-sulfamoylazepine; and 4) by scoring for loss of righting reflex according to the method of Reed-Muench (American Journal of Hygiene, 27: 493–497, 1938), in which mice are administered 12.5 mg./kg. i.p. thioridazine, immediately after which the test compound is administered at dosages of 5 to 100 mg./kg. in a volume of 0.1 ml./10 g. body weight. Sixty minutes after dosing, the mice are scored for loss of righting reflex.

For such uses, the compounds may be combined with one or more pharmaceutically acceptable carriers or adjuvants, and may be administered orally in such forms as tablets, capsules, dispersible powders, granules, syrups, elixirs, suspensions, and the like, or parenterally in the forms of sterile injectable solutions or suspensions. These pharmaceutical preparations may contain up to about 90% of the active ingredient in combination with the carrier or adjuvant. The preferred pharmaceutical compositions from the standpoint of preparation and ease of administration are solid compositions, particularly hard-filled capsules and tablets. Furthermore, the compounds of formula I may be similarly administered in the form of their non-toxic pharmaceutically acceptable salts. Such salts possess the same order to activity as the free base and are readily prepared by reacting the base with an appropriate acid by conventional techniques and, accordingly, are included within the scope of this invention. Representative of such salts are the mineral acid salts, e.g., hydrochloride, hydrobromide, sulfate and the like, and the organic acid salts such as succinate, benzoate, maleate and the like.

The dosage administered will vary depending upon known variables such as the particular compound, the mode of administration and the severity of the condition being treated. For sedative/hypnotic use, in general, satisfactory results are obtained when the compounds are administered at a daily dosage of from about 2 milligrams to about 200 milligrams per kilogram of animal body weight, typically given orally and in a single dose at bedtime. For most large mammals, the administration of from about 150 milligrams to about 1500 milligrams of the compound per day provides satisfactory results with a single dose of from 150 to 1500 milligrams, preferably 150 to 750 milligrams, being given at bedtime. For use as tranquilizers, in general, satisfactory results are obtained when the compounds are administered at a daily dosage of from about 4 milligrams to about 200 milligrams per kilogram of animal body weight, typically given orally and in divided doses, two to four times per day. For most large mammals, the total daily dosage is from about 300 to about 2000 milligrams, and dosage forms suitable for internal administration comprise from about 75 to about 1,000 milligrams, preferably 75 to 500 milligrams, of the compound.

Tablets and capsules containing the ingredients below may be prepared by conventional techniques and are useful for inducing sleep at a dose of one tablet or capsule at bedtime.

| Ingredients | Weight (mg.) | |
| --- | --- | --- |
| | Tablet | Capsule |
| α-methylsulfinyl-4-trifluoro-methyl-o-toluidine | 200 | 200 |
| tragacanth | 10 | — |
| lactose | 247.5 | 300 |
| corn starch | 25 | — |
| talcum | 15 | — |
| magnesium stearate | 2.5 | — |
| Total | 500 mg. | 500 mg. |

Representative formulations of a tablet and a capsule prepared by conventional techniques and useful as minor tranquilizers at a dose of one tablet or capsule 4 times a day are as follows:

| Ingredients | Weight (mg.) | |
| --- | --- | --- |
| | Tablet | Capsule |
| α-methylsulfinyl-4-trifluoro-methyl-o-toluidine | 100 | 100 |
| tragacanth | 10 | — |
| lactose | 197.5 | 250 |
| corn starch | 25 | — |
| talcum | 15 | — |
| magnesium stearate | 2.5 | — |
| Total | 350 mg. | 350 mg. |

The following examples are merely illustrative of specific compounds of the invention and the manner in which they may be prepared.

EXAMPLE 1

α-Methylsulfinyl-4-trifluoromethyl-o-toluidine

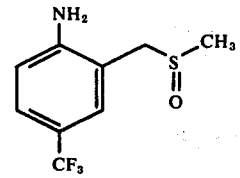

To a cooled (ice/water) solution of 8.7 g. of α-methylthio-4-trifluoromethyl-o-toluidine predissolved in 50 ml. of acetic acid is added 4.1 ml. of a 30% solution of hydrogen peroxide. The ice/water bath is removed and the reaction mixture is stirred for 90 minutes, after which examination by TLC indicates the presence of essentially all of the sulfinyl compound (reaction complete). The reaction mixture is then treated with 50 ml. of a 10% solution of sodium sulfite and concentrated on a rotary evaporator. The residue is then taken up in chloroform and a 15 % solution of sodium hydroxide. After separation of the phases, the aqueous phase is back-extracted with chloroform and the combined chloroform solution is washed successively with water and brine, dried, evaporated in vacuo to dryness, and the residue recrystallized from chloroform/petroleum ether to yield α-methylsulfinyl-4-trifluoromethyl-o-toluidine, m.p. 121.5°–125° C.

EXAMPLE 2

Following the procedure of Example 1, but employing appropriate starting materials in approximately equivalent amounts, the following additional compounds are prepared:

A. α-methylsulfinyl-N-(m-trifluoromethylbenzoyl)-o-toluidine, m.p. 85°–95° C., and B. α-methylsulfinyl-3-trifluoromethyl-o-toluidine, m.p. 88°–93° C.,

What is claimed is:

1. A compound of the formula:

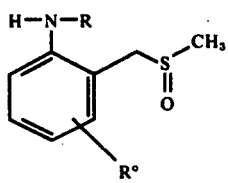

wherein
R° is hydrogen or CF₃, wherein said CF₃ is in the 3- or 4-position of the ring, and
R is hydrogen or meta- or paratrifluoromethyl-benzoyl,
provided that when one of R° and R is hydrogen, the other is other than hydrogen;
or a pharmaceutically acceptable acid addition salt thereof.

2. A compound of claim 1 having the formula

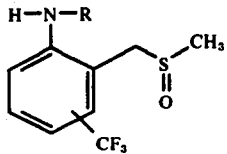

wherein R is as defined in claim 1; or a pharmaceutically acceptable acid addition salt thereof.

3. The compound of claim 2 which is α-methylsulfinyl-4-trifluoromethyl-o-toluidine.

4. The compound of claim 1 which is α-methylsulfinyl-N-(m-trifluoromethylbenzoyl)-o-toluidine.

* * * * *